US005773215A

United States Patent [19]
Hanausek-Walaszek et al.

[11] Patent Number: 5,773,215
[45] Date of Patent: *Jun. 30, 1998

[54] TUMOR MARKER PROTEIN FOR CANCER RISK ASSESSMENT

[75] Inventors: Margaret Hanausek-Walaszek, Bastrop; Thomas J. Slaga, Austin; Zbigniew Walaszek, Bastrop, all of Tex.

[73] Assignee: Board of Regents, The University of Texas System, Austin, Tex.

[*] Notice: The term of this patent shall not extend beyond the expiration date of Pat. No. 5,310,653.

[21] Appl. No.: 405,648

[22] Filed: Mar. 17, 1995

Related U.S. Application Data

[60] Continuation-in-part of Ser. No. 236,547, May 2, 1994, abandoned, which is a division of Ser. No. 12,972, Feb. 2, 1993, Pat. No. 5,310,653, which is a continuation of Ser. No. 426,408, Oct. 24, 1989, abandoned.

[51] Int. Cl.[6] .......................... C12Q 1/68; G01N 33/574
[52] U.S. Cl. .......................... 435/6; 435/7.23; 435/69.3; 536/23.5; 530/352; 530/358; 530/358.8; 530/388.85; 530/389.7; 530/828
[58] Field of Search ............................ 435/6, 69.3, 7.23; 530/352, 358, 828, 388.8, 388.85, 389.7; 536/23.5

[56] References Cited

U.S. PATENT DOCUMENTS

| 4,448,890 | 5/1984 | Smetana et al. | 436/508 |
| 4,746,539 | 5/1988 | Webb et al. | 435/7.23 |

FOREIGN PATENT DOCUMENTS

| 0 462 623 A1 | 12/1991 | European Pat. Off. |
| 0 582 477 A1 | 2/1994 | European Pat. Off. |

OTHER PUBLICATIONS

Result 7, "Human Retinoic Acid Receptor . . . " M57707.
Hanausek-Walaszk et al., "Carcinogenesis," Proceedings of the American Association for Cancer Research 30:190, Abstract 754 (1989).
Larroya et al., "Immunology," Proceedings of the American Association for Cancer Research 30:349, Abstract 1385 (1989).
Hanausek-Walaszek et al., "Carcinogenesis," Proceedings of AACR 29:167, Abstract 665 (1988).
Hanausek-Walaszek et al., "Correspondence Between Biochemical and Antigenic Activity of a 60 Kilodalton Oncofetal Protein During Carcinogenesis and Tumorigenesis," Cancer Letters 33:55–61 (1986).
Hanausek-Walaszek et al., "A 60 Kilodalton Oncofetal Protein As Tumor Marker," J. Med. 17:13–23 (1986).
Schroder et al., "Proteins from rat lover cytosol which stimulate mRNA transport," Eur. J. Biochem. 159:51–59 (1986).
Hanausek-Walaszek et al., "Immunological Identity of a 60 KD Onmcofetal Protein Induced in Rats by Chemical Carcinogens and Released by Transformed Cells," BBRC 127:779–785 (1985).

Hanusek-Walaszek et al., "Chemical carcinogens as specific inducers of a 60–kilodalton oncofetal protein in rats," Carcinogenesis 7:1725–1730 (1985).
Schumm et al., "Abscence of the Cancer–Associated Factor with a Molecular Weight of 60,000 from the Plasma of Patients with a Spectrum of Nonneoplastic Conditions," Cancer Res. 44:401–406 (1984).
Hanausek-Walaszek et al., "Characterization of a 60,000–dalton Oncofetal Protein from the Plasma of Tumor– Bearing Rats," Cancer Invest. 2:433–441 (1984).
French et al., "Nucleocytoplasmic Release of Repetitive DNA Transcripts in Carcinogenesis Correlates with a 60 Kilodalton Cytoplasmic Protein," Cancer Letters 23:45–52 (1984).
Walaszek et al., "An Oncofetal 60–Kilodalton Protein in the Plasma of Tumor–Bearing and Carcinogen–Treated Rats," Cancer Letters 20:277–282 (1983).
Hanausek-Walaszek et al., "Structural and Immunological Identity of p65 Tumor–Associated Factors from Rat and mouse Hepatocarcinomas," Progress in Clinical and Biological Research (1989).
Mirowski et al., "Purification and Characterization of a 65–kDa Tumor–Associated Phosphoprotein from rat Transplantable Hepatocellular Carcinoma 1682C Cell Line," Protein Exp. and Pur. 3:196–203 (1992).
Wang et al., "Monoclonal Antibodies Against a 65–kDa Tumor–Associated Phosphoprotein: Development and Use in Cancer Detection," Hybridoma 12:167–176 (1993).
Mirowski et al., "Demonstration of a 65 kDa Tumor–Specific Phospho–protein in Urine and Serum of Rats with N–methyl–N–nitrosourea–induced Mammary Adenocarcinomas," Carcinogenesis 14:1659–1664 (1993).
Mirowski et al., "Comparative Structural Analysis of Human and Rat 65 kDa Tumor–Associated Phosphoproteins," Int. J. Biochem. 25:1865–1871 (1993).
Del Rio et al., "Expression of a 65 kDa Oncofetal Phosphoprotein in the Altered Hepaic Foci of Rats Fed 2–Acetylaminofluorene Followed by Phenobarbital," Int. J. Oncol. 5:259–265 (1994).
Mirowski et al., "Serological and Immunohistochemical Detection of a 65–kDa Oncofetal Protein in Breast Cancer," European Journal of Cancer 30A:1108–1113 (1994).
Hanausek et al., "The Oncofetal Protein p65 as a New Member of the Steroid/Thyroid Receptor Superfamily," Cancer Detection and Prevention 19:1995, Abstract 118/307 307 (1995).
Mirowski et al., "Isolation of the 65 kDa Oncofetal Phosphoprotein from Fetal Bovine Serum, Polyclonal Antibody Production and use in Cancer Detection," AACR (/toronto, Mar. 20, 1995).
Hanausek et al., "The Oncofetal Protein p65 as a Member of the Steroid/Thyroid Receptor Superfamily: Relevance to Breast Cancer," AACR (Toronto, Mar. 20, 1995).

Primary Examiner—Miichael P. Woodward
Attorney, Agent, or Firm—Arnold, White & Durkee

[57] ABSTRACT

This invention relates to the isolation, identification and sequencing of a cancer associated protein, preparation of hybridization probes therefrom, preparation of antibodies thereto, and methods of cancer risk assessment and diagnosis.

24 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2070 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
GACCCCGAGA  ACGTGAGAGC  CGAGGGCGGG  GACATGAGGG  AGAAAGTGAG  ACTGTCCAGC       60
GCTAGACAGA  GACTGCGATG  CAGCACTAAG  AATAGTCTTC  TCGTTGCTAG  AACATGCGTG      120
CTGAGGCTGG  TCGATTGGAT  CGAGCAGGAT  CTCAAGAGCA  CTTGCGAAAA  GGCTCACGTT      180
TCCCTCCGCG  GGTACCTCGA  ATTGCACCTG  CAATGCGGGA  GACGAAAAGA  GGTTGCCGGG      240
GCTCTGGGTG  GGGATACCAG  ACCTGACCCC  AAGAAGCCGC  GGGGGGGCTC  CAAAAAGAAC      300
GTGGAGGACA  CCCTTGTCAA  AGACAAGCTG  AGCCCAAGTA  GCGCGGTTTG  CGAGTCCCCC      360
GAGGTGTATG  GTGATGACGT  AGGCTCTCAG  GCTGCGGACA  GCCCGAGGAA  ACAGCTGGCC      420
GCGAAAGGGA  CATTCAGAGA  TAAGGACAAA  ATTGAAGCGC  TGTTCAAGCT  CGGGGAGCTG      480
GTGGCTAAAA  AAGCCTTGTC  CTCAGCAATT  ACTTGGTTCC  CCAACAGCGT  GTCGCCTCTA      540
CACGCCCATT  ATGGCGATGA  AATCCTCTAC  AAGGATGAAT  CCGGGCTTGT  CAACATTAGC      600
GAGGGTGGCA  AAAGAGGCGT  GGAGATCCAC  CCCCCAGATA  ACTTCGGCAT  CACAACCCTT      660
GATGAAGATC  TTGGCTTTCC  CCAAATAATT  GTGATTAACG  TGAAGCCTCA  AACCGAGGAA      720
GCCAACACTT  GGTAAAGACA  GGATCTGAAA  TATCATAACA  GTGCAAACGA  GGCCGGGTAC      780
TCCGACGAGA  ATAAAACCTT  TGTGAGAGGA  TGTAGAAAAG  ATGGGCATAG  TGAGCGTAAC      840
AATATGACCA  CAGGTGACAG  AAATTCAAAA  AAGGCCCAGC  CCGTAAACTT  CTCCCTCATG      900
GCATCCCTCG  CCCTGGATTC  TAGGGGCAAA  GCCGCGGGGC  CCCGGCGCGG  AGCGAGGCGC      960
CTGTGCCTGG  TGTGTGAGGA  CTATGCCAGC  TGTTCAAACA  CCTGTGTCTG  GTCCTGTGAA     1020
GCCTACAAGG  TCTTCTTTCG  CCGAAGTCAG  GGAAACACAG  ACTACTATTG  TTTCACAAAC     1080
GATTGCAACA  TCTCTAAGAA  TAGATCTAAG  TCTTGCCCAG  CCTGCCTCCT  TCGTTGCCTG     1140
CACCCTAGCA  TCAATGAGAT  CCGAAAAGAC  AAGCGAGCAG  CGCTGAATGT  GCGAGACAAC     1200
GTTGGTGAAG  AGGTGGATAT  GACCGGTCCT  AGCTGGACCT  GCCTGAAGCT  ACTCTTTTCA     1260
GATGGAGAAA  AAGTGATACC  CAGATTGGCC  CATGAACTTC  CAGGGATCAA  GCGTGGCCGG     1320
```

```
CAGGCACAAC AGCAGTCCCA CCGAGGAAGC CCCATTCCCA AAAAGAGGAA AGGTTGGCCT      1380

CCTGGACATG TCCTGTCAAA TGACCGCGCA GCTGCTGGCA CGGTATGGAA ACCAAAATCC      1440

TGTGAACCAA TTCGCCGAGA AGGCCCCAAG TGGGACGCTC GGCTGAATGA ATCTACCACC      1500

TTTGTTTTGG GGTCTCGAGC CAACAAGGCC TTAGGGAAGG GAGGCACCAG AGGGAGGATT      1560

TACATCAAGC ACCCACACCT CTTTAAGTAT GCAGCAGATC CTCAGGACAA GCACTGGCTG      1620

GCTGAGCAGC ATCATCGGCA GCGGTTCGCA GAATTGCTTC TCAAGATTAG CCATATTAGG      1680

CACATGGTTG AGGGAGTGGC TCATTGCTTG TACGACATGA AAGTTAAGGA CAAAGTTCTG      1740

CCATCCTGGA AGGTTGAGAA GTTGCGGAAA TACGTGGAGA CACTACGGAC AGAAAATGAG      1800

CATCGTGTCG CTGAAGCAAG TCCCCAGACC TGAGCCGAGT GTCCTGGTCT ACTACACTTG      1860

CAGTCTGCCT CCCAGACCCT CTTTCCCGGC CCGGCTGAGG CCATCATGGG GATGCGGTCT      1920

AGTTGGCTCT TAGCAGCAAT CAAGCGTTAC ATGAGCTAGT TTGTAGTGAC TCACTGCAGA      1980

GCCCCCAGAC TGGCTTGTGG TTCTGTTTCT AAAGTTATTG GAATAAGAAG CAATTAAACA      2040

AGTTTGTAAT TTAAAAAAAA AAAAAAAAA                                        2070
```

(2) INFORMATION FOR SEQ ID NO:2:

(i) SEQUENCE CHARACTERISTICS:
        (A) LENGTH: 691 amino acids
        (B) TYPE: amino acid
        (C) STRANDEDNESS: single
        (D) TOPOLOGY: linear     (ii) MOLECULE TYPE: protein     (ix) FEATURE:
        (A) NAME/KEY: Modified-site
        (B) LOCATION: 612
        (D) OTHER INFORMATION: /note= "Xaa = Unknown"

(ix) FEATURE:
        (A) NAME/KEY: Modified-site
        (B) LOCATION: 654
        (D) OTHER INFORMATION: /note= "Xaa = Unknown"

(ix) FEATURE:
        (A) NAME/KEY: Modified-site
        (B) LOCATION: 680
        (D) OTHER INFORMATION: /note= "Xaa = Unknown"

(ix) FEATURE:
        (A) NAME/KEY: Modified-site
        (B) LOCATION: 684
        (D) OTHER INFORMATION: /note= "Xaa = Unknown"

(xi) SEQUENCE DESCRIPTION: SEQ ID NO:2:

```
Met Asp Pro Glu Asn Val Arg Ala Glu Gly Gly Asp Met Arg Glu Lys
 1               5                  10                  15

Val Arg Leu Ser Ser Ala Arg Gln Arg Leu Arg Cys Ser Thr Lys Asn
            20                  25                  30

Ser Leu Leu Val Ala Arg Thr Cys Val Leu Arg Leu Val Asp Trp Ile
        35                  40                  45

Glu Gln Asp Leu Lys Ser Thr Cys Glu Lys Ala His Val Ser Leu Arg
    50                  55                  60

Gly Tyr Leu Glu Leu His Leu Gln Cys Gly Arg Arg Lys Glu Val Ala
65                  70                  75                  80

Gly Ala Leu Gly Gly Asp Thr Arg Pro Asp Pro Lys Lys Pro Arg Gly
                85                  90                  95

Gly Ser Lys Lys Asn Val Glu Asp Thr Leu Val Lys Asp Lys Leu Ser
           100                 105                 110
```

```
Pro  Ser  Ser  Ala  Val  Cys  Glu  Ser  Pro  Glu  Val  Tyr  Gly  Asp  Asp  Val
          115                 120                      125

Gly  Ser  Gln  Ala  Ala  Asp  Ser  Pro  Arg  Lys  Gln  Leu  Ala  Ala  Lys  Gly
130            135                           140

Thr  Phe  Arg  Asp  Lys  Asp  Lys  Ile  Glu  Ala  Leu  Phe  Lys  Leu  Gly  Glu
145                 150                 155                                160

Leu  Val  Ala  Lys  Lys  Ala  Leu  Ser  Ser  Ala  Ile  Thr  Trp  Phe  Pro  Asn
               165                      170                           175

Ser  Val  Ser  Pro  Leu  His  Ala  His  Tyr  Gly  Asp  Glu  Ile  Leu  Tyr  Lys
               180                 185                           190

Asp  Glu  Ser  Gly  Leu  Val  Asn  Ile  Ser  Glu  Gly  Gly  Lys  Arg  Gly  Val
          195                      200                 205

Glu  Ile  His  Pro  Pro  Asp  Asn  Phe  Gly  Ile  Thr  Thr  Leu  Asp  Glu  Asp
          210                 215                      220

Leu  Gly  Phe  Pro  Gln  Ile  Ile  Val  Ile  Asn  Val  Lys  Pro  Gln  Thr  Glu
225                      230                 235                           240

Glu  Ala  Asn  Thr  Trp  Leu  Arg  Gln  Asp  Leu  Lys  Tyr  His  Asn  Ser  Ala
               245                      250                           255

Asn  Glu  Ala  Gly  Tyr  Ser  Asp  Glu  Asn  Lys  Thr  Phe  Val  Arg  Gly  Cys
               260                 265                           270

Arg  Lys  Asp  Gly  His  Ser  Glu  Arg  Asn  Asn  Met  Thr  Thr  Gly  Asp  Arg
          275                      280                      285

Asn  Ser  Lys  Lys  Ala  Gln  Pro  Val  Asn  Phe  Ser  Leu  Met  Ala  Ser  Leu
     290                 295                      300

Ala  Leu  Asp  Ser  Arg  Gly  Lys  Ala  Ala  Gly  Pro  Arg  Arg  Gly  Ala  Arg
305                 310                      315                           320

Arg  Leu  Cys  Leu  Val  Cys  Glu  Asp  Tyr  Ala  Ser  Cys  Ser  Asn  Thr  Cys
               325                      330                           335

Val  Trp  Ser  Cys  Glu  Ala  Tyr  Lys  Val  Phe  Phe  Arg  Arg  Ser  Gln  Gly
               340                 345                           350

Asn  Thr  Asp  Tyr  Tyr  Cys  Phe  Thr  Asn  Asp  Cys  Asn  Ile  Ser  Lys  Asn
          355                      360                      365

Arg  Ser  Lys  Ser  Cys  Pro  Ala  Cys  Leu  Leu  Arg  Cys  Leu  His  Pro  Ser
     370                 375                      380

Ile  Asn  Glu  Ile  Arg  Lys  Asp  Lys  Arg  Ala  Ala  Leu  Asn  Val  Arg  Asp
385                      390                      395                      400

Asn  Val  Gly  Glu  Glu  Val  Asp  Met  Thr  Gly  Pro  Ser  Trp  Thr  Cys  Leu
                    405                      410                           415

Lys  Leu  Leu  Phe  Ser  Asp  Gly  Glu  Lys  Val  Ile  Pro  Arg  Leu  Ala  His
               420                      425                      430

Glu  Leu  Pro  Gly  Ile  Lys  Arg  Gly  Arg  Gln  Ala  Gln  Gln  Ser  His
          435                      440                      445

Arg  Gly  Ser  Pro  Ile  Pro  Lys  Lys  Arg  Lys  Gly  Trp  Pro  Pro  Gly  His
     450                      455                      460

Val  Leu  Ser  Asn  Asp  Arg  Ala  Ala  Ala  Gly  Thr  Val  Trp  Lys  Pro  Lys
465                      470                      475                      480

Ser  Cys  Glu  Pro  Ile  Arg  Arg  Glu  Gly  Pro  Lys  Trp  Asp  Ala  Arg  Leu
                    485                      490                      495

Asn  Glu  Ser  Thr  Thr  Phe  Val  Leu  Gly  Ser  Arg  Ala  Asn  Lys  Ala  Leu
               500                      505                      510

Gly  Lys  Gly  Gly  Thr  Arg  Gly  Arg  Ile  Tyr  Ile  Lys  His  Pro  His  Leu
          515                      520                      525

Phe  Lys  Tyr  Ala  Ala  Asp  Pro  Gln  Asp  Lys  His  Trp  Leu  Ala  Glu  Gln
```

|     |     |     |     | 530 |     |     |     |     |     | 535 |     |     |     |     |     | 540 |     |     |     |
| --- | --- | --- | --- | --- | --- | --- | --- | --- | --- | --- | --- | --- | --- | --- | --- | --- | --- | --- | --- |
| His 545 | His | Arg | Gln | Arg | Phe 550 | Ala | Glu | Leu | Leu | Leu 555 | Lys | Ile | Ser | His | Ile 560 |
| Arg | His | Met | Val | Glu 565 | Gly | Val | Ala | His | Cys 570 | Leu | Tyr | Asp | Met | Lys 575 | Val |
| Lys | Asp | Lys | Val 580 | Leu | Pro | Ser | Trp | Lys 585 | Val | Glu | Lys | Leu | Arg 590 | Lys | Tyr |
| Val | Glu | Thr 595 | Leu | Arg | Thr | Glu | Asn 600 | Glu | His | Arg | Val | Ala 605 | Glu | Ala | Ser |
| Pro | Gln 610 | Thr | Xaa | Ala | Glu | Cys 615 | Pro | Gly | Leu | Leu | His 620 | Leu | Gln | Ser | Ala |
| Ser 625 | Gln | Thr | Leu | Phe | Pro 630 | Gly | Pro | Ala | Glu | Ala 635 | Ile | Met | Gly | Met | Arg 640 |
| Ser | Ser | Trp | Leu | Leu 645 | Ala | Ala | Ile | Lys | Arg 650 | Tyr | Met | Ser | Xaa | Phe 655 | Val |
| Val | Thr | His | Cys 660 | Arg | Ala | Pro | Arg | Leu 665 | Ala | Cys | Gly | Ser | Val 670 | Ser | Lys |
| Val | Ile | Gly 675 | Ile | Arg | Ser | Asn | Xaa 680 | Thr | Ser | Leu | Xaa | Phe 685 | Lys | Lys | Lys |
| Lys | Lys 690 | Lys |     |     |     |     |     |     |     |     |     |     |     |     |     |

TUMOR MARKER PROTEIN FOR CANCER RISK ASSESSMENT

RELATED APPLICATION

The present application is a continuation-in-part of U.S. patent application Ser. No. 08/236,547, filed May 2, 1994, abandoned, which was a divisional application of U.S. patent application Ser. No. 08/012,972, filed Feb. 2, 1993, issued as a U.S. Pat. No. 5,310,653 on May 10, 1994, which was a continuation of U.S. patent application Ser. No. 07/426,408, filed Oct. 24, 1989, abandoned.

GOVERNMENT RIGHTS

The United States Government may have certain rights to this invention pursuant to National Institutes of Health grants RR 5511-23 and CA 54296.

FIELD OF THE INVENTION

This invention relates to the isolation, identification and sequencing of a cancer associated protein, preparation of hybridization probes therefrom, preparation of antibodies thereto, and methods of cancer risk assessment and diagnosis.

BACKGROUND OF THE INVENTION

In spite of improved treatments for certain forms of cancer, it is still a leading cause of death in the United States. Since the chance for complete remission of cancer is, in most cases, greatly enhanced by early diagnosis, it is very desirable that physicians be able to detect cancers before a substantial tumor develops. Also, in cases where the primary tumor has been substantially removed by surgery or destroyed by other means, it is important that the physician be capable of detecting any trace of cancer in the patient (either in the form of residues of the primary tumor or of secondary tumors caused by metastasis), in order that the physician can prescribe appropriate subsequent treatment, such as chemotherapy.

The quantities of cancer cells that must be detected for early diagnosis or following removal or destruction of the primary tumor are so small that the physician cannot rely upon physical examination of the cancer site. Moreover, in many cases the cancer site is of course not susceptible to direct visual observation and it is almost always impractical to detect secondary tumors by visual observation, since it is not possible to predict exactly where they are likely to occur. Accordingly, sensitive tests have to rely upon detection of cancer-associated materials, usually proteins, present in body fluids of patients who have, or are about to develop, cancer cells in their bodies. Several diagnostic materials for detection of cancer-associated proteins are available commercially. Tests for alpha-fetoprotein are used to detect primary liver cancer and teratocarcinoma in humans; and carcinoembryonic antigen is used for digestive system cancers, as well as lung and breast carcinomas; chorionic gonadotropin is employed to detect trophoblast and germ cell cancers; calcitonin is used for thyroid gland cancers; and prostatic acid phosphatase or prostate specific antigen are used to detect prostate carcinoma. These markers are detectable in advanced rather than in early cancer.

Unfortunately, many of the commercially available tests are only applicable to a narrow range of cancer types, and therefore these tests suffer not only from the disadvantage that other types of cancer may be missed but also from the disadvantage that the narrow applicability of the tests means that it may be necessary to run multiple tests on a single patient for diagnostic purposes, a procedure which not only increases the expense of the diagnostic testing but also increases the risk that one or other of the tests may give a false positive result. Accordingly, there is a need for a single diagnostic test able to detect the presence of very small amounts of cells of a wide variety of different cancers. The ideal marker would be one that is specific and universal. Such a marker may exist if malignant transformation is associated with the expression of a unique gene product in all kinds of transformed cells.

It is already known that serum from the blood of animals suffering from a wide variety of cancers contains an oncofetal protein having a molecular weight of approximately 60,000 and having the capacity to increase the release of ribonucleic acid (RNA) from cell nuclei. This protein is referred to as oncofetal RNA-transport protein (ORTP) or 60 kDa cancer-associated protein.

ORTP is localized in the cytoplasm of tumors of humans and experimental animals and small amounts are released into the host circulatory system. The 60 kDa ORTP is notably absent from the nuclei of rat liver and rat liver tumors. It has been shown to be present in fetal rats at 18 days of gestation and in human and rat amniotic fluid, but not in maternal blood. It has not been detected in adult rats. Nor is it present in detectable concentrations in the blood of normal human subjects or those with a variety of non-neoplastic conditions or diseases, including benign tumors and other non-neoplastic proliferative diseases. In contrast, of more than 200 cancer patients with confirmed active disease, all tested positive for the factor. It was also present in all of about 200 tumor-bearing rats tested. Unfortunately, antibodies to a rat ORTP preparation purified as described in the prior art do not cross-react with human ORTP. Thus, the 60 kDa cancer marker proteins from different species are not immunologically equivalent, e.g., an antibody to the rat cancer marker protein does not cross-react with a human cancer marker protein. Thus, when the purified 60 kDa cancer marker protein preparation is to be used for production of antibodies for diagnostic purposes, it is necessary to begin the preparation process with plasma from the species in which the diagnosis is to be used.

We have recently identified, characterized in terms of its physical properties, and sequenced another oncofetal protein with a molecular weight of 65 kDa (p65) which exhibits certain properties which strongly favor its candidacy as a general tumor marker, as well as a marker of cancer risk associated with the prolonged use of drugs, such as androgenic and estrogenic hormones, that have tumor promotional potential.

This newly isolated and sequenced 65 kDa oncofetal protein, termed p65, exhibits properties desirable for a marker of pre-malignant and malignant alterations. The p65 protein is a novel protein that appears to have some homology to the steroid receptor superfamily of genes. Therefore, the p65 gene may belong to a family of genes which encode nuclear receptors, composed of several domains important in hormone binding, DNA-binding, dimerization, and activation of transcription for various hydrophobic ligands such as steroids, vitamin D, retinoic acid and thyroid hormones. More support for this theory is evident by the discovery that the p65 protein is located in nuclei of tumor cells and has DNA-binding properties. Alterations in hormone receptors such as estrogen (ER) and progesterone receptor (PR) may be of prognostic significance in breast cancer; therefore, elucidation of whether p65 is related to ER or PR is of utmost importance. Elevated serum levels of p65 are detectable by ELISA in 90% of patients with stage I-IV of breast cancer and limited immunohistochemical studies have shown nuclear and cytoplasmic expression in 80% of breast cancer biopsies. In depth study of the p65 protein is thus helpful in understanding the mechanisms by which hormones and their respective receptors regulate the metabolism of normal and malignant breast and prostate cancer as well as other cancers.

The present invention, specifically the elucidation of p65's sequence can be utilized for the detection, diagnosis and hopefully, the future treatment of breast, prostate, ovarian and possibly other cancers that relate to the steroid receptor superfamily of genes.

SUMMARY OF THE INVENTION

This invention provides a protein preparation containing a pure form of a newly discovered oncofetal cancer marker protein encoded by the nucleic acid sequence SEQ ID NO: 1 and having the amino acid sequence of SEQ ID NO: 2. More specifically, the invention provides the sequence of and methods of using the nucleic acid sequence SEO ID NO: 1 and the rat p65 cancer-associated protein having the amino acid sequence SEQ ID NO:2 for the preparation of hybridization probes and antibodies to be used for the detection of cancer.

One embodiment of the present invention provides a nucleic acid molecule of less than 2200 base pairs in length coding for the rat p65 protein. An aspect of this embodiment provides the DNA segment comprising a sequence region having the sequence of SEQ ID NO: 1. Another aspect provides the analogous RNA segment. And yet a further aspect provides the amino acid sequence having the sequence of SEQ ID NO: 2.

The invention also provides that the DNA segment comprising a sequence region having the sequence of SEQ ID NO: 1 be placed under the control of a promoter. The DNA segment can also be placed into a plasmid and additionally into a recombinant host cell.

The present invention further provides a method of using the DNA segment having the sequence of SEQ ID NO: 1 to make the encoded rat p65 comprising:
  (a) preparing a recombinant vector in which the sequence of SEQ ID NO: 1 is positioned under the control of a promoter;
  (b) introducing the recombinant vector into a host cell to form a recombinant host cell;
  (c) culturing the recombinant host cell under conditions effective to allow expression of the protein; and
  (d) collecting the expressed protein.

The invention additionally provides a recombinant rat p65 protein prepared by expressing the rat p65 protein in a recombinant host cell and purifying the protein.

In another embodiment, the present invention provides a sequence region complementary to a region of at least 10–14 contiguous nucleotides of SEQ ID NO: 1.

The invention further provides a method for detecting p65 and oncofetal protein in a sample of mammalian origin comprising:
  (a) obtaining nucleic acids from a sample suspected of containing the p65 protein;
  (b) contacting the sample nucleic acids with a nucleic acid segment of at least 10–14 nucleotide long continuous sequence that is complementary to a contiguous sequence of SEQ ID NO: 1 under appropriate conditions for hybridization; and
  (c) detecting the hybridized nucleic acids thus formed.

In one aspect of the aforementioned embodiment the sample nucleic acids are located within a cell such as in the case of in situ hybridization. Alternatively, the sample nucleic acids are separated from a cell and then tested for the presence of a sequence complementary to the 10–14 nucleotide long sequence. The nucleic acids to be tested can be of DNA (Southern blotting) or RNA (Northern blotting).

Finally, this invention provides a method for assessing the likelihood of cancer which involves immunoassays and hybridization assays to detect the presence of the instant p65 tumor marker protein in biological material of a host suspected of developing cancer or being at high risk for developing cancer as the result of treatment with drug(s) known to have a tumor promotion potential.

BRIEF DESCRIPTION OF THE DRAWINGS

FIG. 1 shows p65 tumor-associated protein production during 7,12-dimethylbenz[a]anthracene (DMBA)-induced, and 12-0-tetra-decanoylphorbol-13-acetate (TPA)-promoted skin carcinogenesis in SENCAR mice.

DETAILED DESCRIPTION OF THE PREFERRED EMBODIMENTS

Methods for Diagnosing or Assessing the Likelihood of Cancer

Samples of blood plasma or serum tissue are obtained from human cancer patients or human subjects prior to and at different times in the course of treatment with synthetic steroid hormones or other drugs known or suspected of having a tumor promotion potential. Alternatively, samples of blood plasma, serum or tissue are obtained from other mammals suspected of suffering from cancer or treated with substances suspected of causing cancer.

Briefly, samples of the blood plasma or serum containing the same amount of protein are mixed with an electrophoresis sample buffer, boiled for three minutes and subjected to 12.5% SDS-PAGE. Subsequently, the gel slabs are prepared for transfer by equilibrating for one hour in 0.025M Tris, 0.192M glycine, 20% (v/v) methanol, pH 8.3, and then transblotted onto nitrocellulose sheets. To conduct the immunoassay, the nitrocellulose sheets are treated with appropriate blocking solution to block unspecific binding sites and incubated overnight, either with pre-immune serum (controls) or antibody against the p65 protein diluted 1:200. Secondary biotinylated antibody is applied next and the color is developed using ABC Elite Kit from Vector Laboratories, Burlingame, Calif. The highly specific polyclonal antibody against p65 is obtained by immunizing rabbit with pure human or rat p65 preparations. As an alternative, mouse monoclonal antibodies to p65 may be prepared using the techniques generally described in "Hybridoma Techniques" Cold Spring Harbor, N.Y., 1980, ISBN 0-87969-143-3.

The immunoblots are photographed and the bands of p65 immune complexes on the film are quantitated using a laser densitometer coupled to an integrator. Alternatively, following probing with the antibodies to p65 or pre-immune serum, nitrocellulose sheets are labeled with $^{125}$I-protein A. The labeled sheets are subjected to autoradiography followed by scanning the film with a laser densitometer coupled to an integrator. Another alternative is to use an ELISA procedure.

To interpret the plasma or serum or tissue samples, the relative quantity of p65 in the sample is indicated by the intensity of a band at nominal molecular weight about 65,000 as measured by laser scanning. Comparison with the corresponding area of the control (derived with the use of pre-immune serum) permits distinguishing response specific for p65 above non-specific background response. Specific activity of the marker band from clinical samples taken in the course of treatment is compared with the samples taken prior to treatment and/or with the average sample from a normal healthy pool. The clinical response can be then expressed as a factor against the response prior to treatment or against the response of the normal healthy pool, respectively. Steady increases in the value of clinical response over a period of time are indicative of an increased cancer risk associated with the long-term treatment with a given synthetic steroid or other drug that has tumor promotional properties. The high initial response is indicative of an existing cancer.

EXAMPLE I

Animal Models for Determination of the Presence of Cancer Cells

This example illustrates the instant process for purification of the p65 tumor-associated protein and preparation of antibodies thereto as source of p65.

Rat and Mouse Liver Tumors

Rat hepatoma cell lines McA-RH7777 and McA-RH8994 were purchased from the American Type Culture Collection (Rockville, Md.) and carried as cell cultures in Swim's S77 medium with 4 mM L-glutamine and supplemented with 5% fetal calf serum and 20% horse serum (Gibco, Grand Island, N.Y.). After several passages in cell culture, rat hepatoma cells ($1 \times 10^6$/0.2 ml phosphate-buffered saline) were inoculated subcutaneously into a hind leg of male Buffalo rats (120–150 g) (Harlan Labs, Indianapolis, Ind.) and were carried as solid tumors according to conventional procedures.

Transplantable hepatocellular carcinoma (THC) 1682C was derived from primary hepatic tumors in ACI rats maintained for four months on the choline-deficient diet of Shinozuka containing 0.2% ethionine and eight months on a choline-supplemented (0.8%) diet without ethionine. THC T52 was established by intraperitoneal transplantation of growing tumors induced in ACI rats by 2-acetylaminofluorene (AAF). THC cultures were maintained in vitro and also carried as solid (1682C) and ascitic (T52) tumors in male ACI rats (The University of Texas M.D. Anderson Cancer Center Science Park-Veterinary Resources Division, Bastrop, Tex.).

The Reuber hepatoma cell culture H35 was provided by Dr. Andrew P. Butler, University of Texas M.D. Anderson Cancer Center Carcinogenesis Department, Science Park, Smithville, Tex.

Mouse liver carcinoma CRL 6421 (formerly NBL #MM45T.Li) was obtained from American Type Culture Collection and carried as cell cultures as described above for rat hepatoma cell lines.

Purification of p65

Preparation of the antibody involves purification of the p65 marker protein from the tissue culture medium of tumor cells of human or animal origin. Specifically, the cells were grown to confluence at 37° C. in the presence of media and a serum or serum-like supplement, or completely defined medium containing salts and hormones. Growing cells to confluence was a purely economical step which ascertains a high yield of the p65 marker protein. The preferred medium used was Dulbeccols Modified Eagle's Medium (DMEM) with 5% fetal calf serum and cells were grown in 5% $CO_2$. The confluent cells were washed three times in serum-free DMEM medium and incubated in this medium for 16–24 hours (the optimal time being 24 hours). At this point, medium was collected by centrifugation at 10,000 x g for 10–15 minutes and treated with ammonium sulfate solution at 90% saturation of aqueous solution for 30 minutes at 4° C.

Protein precipitate was collected by 30-minute centrifugation at 10,000x g, dissolved in a small volume of 50 mM Tris-Cl buffer, pH 7.5, with 50 mM NaCl, 10 mM 2-mercaptoethanol and 1 mM EDTA, and dialyzed overnight against the same buffer. After dialysis, proteins were loaded on an LKB TSK 3000 SW molecular sieving column and separated according to the molecular weight using an LKB HPLC system. Fractions containing proteins with molecular weight in the range of 50–90 kDa were collected and dialyzed overnight against buffer A, containing 20% ammonium sulfate in 50 mM Tris-Cl, pH 7.5 with 10 mM 2-mercaptoethanol and 1 mM EDTA.

Following dialysis, the 50–90 kDa proteins were loaded on a phenyl hydrophobic interaction column (PHI) (LKB, Pharmacia) equilibrated with buffer A. Generally, 800–1,000 ml of conditioned medium was processed as described above. The p65 marker protein weakly binds to the PHI column and is eluted in the first distinct peak by a gradient of 80% to 0% of buffer A, in combination with buffer B (50 mM Tris-Cl, pH 7.5 with 10 mM 2-mercaptoethanol and 1 mM EDTA, supplemented with 50% ethylene glycol). Fractions containing the p65 marker protein are then combined and dialyzed against buffer A devoid of ammonium sulfate, concentrated by lyophilization and electrophoresed on 12.5% SDS-PAGE at constant current of a 10 mA for two hours at room temperature.

Proteins are transblotted to a $0.22\mu$ nitrocellulose sheet as described by Towbin et al. (Proc. Natl. Acad. Sci. U.S.A., Vol. 76, pages 4350–4353, 1979). A reversible Ponceau A stain was used to visualize the nitrocellulose bound proteins according to the procedure of Salinovich and Montellaro (Anal. Biochem., Vol. 156, pages 341–347, 1986). The band of the p65 protein was cut out of the nitrocellulose sheets and used for immunization of rabbits.

Mouse p65 was isolated from the mouse liver carcinoma cell line CRL 6421 (MM45) and purified as described above for the rat factor.

Preparation of Antibodies to p65

Antisera to the purified rat p65 preparation were raised in rabbits, as follows.

Specific Pathogen Free (Pasteurella) male New Zealand white rabbits of approximately four kilograms body weight were used (Myrtle Is Rabbitry). Pre-immune (day 0) and test blood samples (10 days following each of four immunizations on day 1, 14, 28 and 42) were obtained from the central artery of the ear or a lateral ear vein. The anesthetized rabbits were placed in sternal recumbency, the dorsal fur was removed with surgical clippers, and the surgical site was aseptically prepared with provodine-iodine (Wescodyne, West Chemical) followed by 70% ethanol. Six incisions about 1.0 cm each were made in an anteroposterior direction through the skin and subcutis with a scalpel. The incisions were undermined with blunt and sharp dissection to allow implant placement over the superficial epaxial musculature. The nitrocellulose strip containing the rat p65 protein was cut into six pieces (each approximately 0.5 cm×1.5 cm) which were then formed into rolls for insertion. Following placement, the skin edges were opposed with tissue forceps and closed with surgical adhesive (Vetbond, 3M). Adequate spacing (about 2.5 cm) between insertion fields will allow subsequent immunization incisions to be made adjacently. Terminal blood collection was made in Alsever's solution in anesthetized rabbits by the use of a vacuum assisted collection device to provide the serum which is the polyclonal antibody source. The antisera were absorbed with normal plasma proteins immobilized on nitrocellulose sheets following its electrophoresis on 10% SDS-PAGE and transblotting. An ELISA assay or immunoblotting analysis was conducted to determine the potency and specificity of the antisera obtained.

A standard ELISA procedure was used for detection of specific antibodies in serum. Ninety-six well microliter plates designed for ELISA were used (Immunol 2, Dynatech). For detection of rabbit anti-p65 antibodies, the ELISA plates were pre-coated with several different concentrations of antigen. To test sera, a positive reference serum and a negative pre-immune serum were added to the wells in five-fold dilutions in PBS. Anti-p65 antibodies were detected by goat anti-rabbit IgG conjugated with horse radish peroxidase (Bio-Rad). After the substrate reaction, plates were read on an ELISA plate reader at 405 nm (Litton Bionetics, Laboratory Product Division, South Carolina). A serum sample was considered positive when it read 0.05 units or more above the background.

Probing of Western blots with prepared antibody was carried as follows.

The purified rat tumor-associated protein, p65, was separated by PAGE and electrophoretically transferred to nitrocellulose as described above. Free binding sites on the nitro-cellulose sheets were then blocked overnight using 1% normal goat serum in TTBS buffer (0.5% Tween, 0.1 mM Tris-HCl, pH 7.1, 09% saline). Antisera obtained from immunized rabbits were diluted serially in the blot buffer (TTBS) and incubated with the nitro- cellulose strips for one hour at room temperature. The blots were then washed with several changes of TTBS buffer containing 1% goat serum.

Bound antibody was detected using biotinylated second antibody (goat anti-rabbit IgG, biotinylated) and the avidin-biotin-peroxidase method (Vectastain ABC Elite, Vector, Burlingame, Calif.). To develop blots, 0.02% hydrogen peroxide was used, mixed with 0.1% diaminobenzidine tetrachloride (DAB) made in 0.1M Tris-HCl buffer, pH 7.2. Color generally developed within five to ten minutes; blots were rinsed with distilled water and air dried to preserve color.

Alternatively, bound antibody was detected by incubating the nitrocellulose strips with $^{125}$I-Protein A ($1 \times 10^6$ cpm/ml of blot buffer). After a 60-minute incubation, unbound label was removed by repeated washes of the blots with PBS buffer containing 0.5% Tween. The bound antigen $^{125}$I-Protein A complex was detected by overnight autoradiography using Kodak X-OMAT-AR film.

In addition, monoclonal antibody preparations can be made to the 65 kDa cancer marker by employing conventional techniques well known to the art.

EXAMPLE II

SDS-PAGE and Immunoblotting Analyses

Carefully dissected hepatomas (see Example I) and liver fragments from normal rats and mice were rinsed with an ice-cold saline solution and processed for immunochemical determination of p65. Liver tumor cells grown in culture, as described in Example I, were separated from medium by centrifugation, rinsed with the cold saline solution, and processed for immunoassay of the p65 tumor-associated factor. Briefly, small pieces of tissues or tumor cell pellets were homogenized in TMK-sucrose buffer, pH 7.2, and samples of the total homogenate containing the same amount of protein were mixed with electrophoresis sample buffer, boiled for three minutes, and subjected to 10% SDS-PAGE. The proteins precipitated at 90% saturation of ammonium sulfate from the conditioned medium of hepatocarcinoma cells were dissolved in TMK buffer and electrophoresed in a similar manner. Subsequently, the gel slabs were prepared for transfer by equilibration for one hour in 0.025M Tris, 0.192M glycine, 20% methanol (vol/vol), pH 8.3, and then transblotted onto nitrocellulose sheets.

For immunoassay, the nitrocellulose sheets were treated with the appropriate blocking solution to block non-specific binding sites and incubated overnight, either with pre-immune serum (controls) or antibody against rat p65 diluted 1:200. Secondary biotinylated antibody was applied next, and the color was developed Kit (Vector Laboratories, Burlingame, Calif.). The highly specific polyclonal antibody against p65 was obtained by immunizing rabbits with the rat p65 preparation purified as described above.

Presence of p65 in Rat and Mouse Liver Tumors and its Absence from Normal Mouse and Rat Liver When total protein samples from rat and mouse liver carcinomas grown in vitro were analyzed by SDS-PAGE and then anti-rat p65 antibody probing of Western blots, a single, prominent band was detected in the 65 kDa region of the blots. Some weak bands seen in the 60–64 kDa region may represent degradation products of the native species of p65. Other minor bands resulted from non-specific staining. There is no band characteristic of p65 in immunoblots representing normal adult rat or mouse liver.

All hepatocarcinoma cells grown in vitro as cell cultures and tumor tissues from Morris hepatomas carried as solid tumors in vivo were positive for the p65 antigen. There was no reaction with normal liver cells of either rat or mouse origin. Thus, immunoblotting analysis has demonstrated that p65 was specifically produced by liver cancer cells but not by the cells of normal adult rat or mouse liver.

EXAMPLE III

Interspecies cross-reactivity of Antibodies Against p65

The p65 tumor-associated factors derived from different species are immunologically cross-reactive.

TABLE 1

Immunoprecipitation of p65 from Different Sources by Antibodies Raised in Rabbits against Rat p65.

| Source of p65 | Immunoprecipitation of p65[a] |
|---|---|
| Plasma: | |
| Morris Hepatoma 7777-bearing Rats | +++ |
| Morris Hepatoma 8994-bearing Rats | +++ |

TABLE 1-continued

Immunoprecipitation of p65 from Different Sources by Antibodies
Raised in Rabbits against Rat p65.

| Source of p65 | Immunoprecipitation of p65[a] |
|---|---|
| Pregnant Rats | – |
| Normal Rats | – |
| Cytosol: | |
| Morris Hepatoma 7777 Tumors | +++ |
| Morris Hepatoma 8994 Tumors | +++ |
| Normal Rat Liver | – |
| Conditioned Culture Medium: | |
| Morris Hepatoma 7777 Cells | +++ |
| Morris Hepatoma 8994 Cells | +++ |
| Rat THC 1682 Cells | +++ |
| Mouse Squamous Cell Carcinoma | ++ |
| Human Breast Cancer Cells (MCF-7) | ++ |
| Unconditioned Culture Medium | – |

*+++ = over 90% precipitation; ++ = 50–90% precipitation
– = less than 25% precipitation The p65 activity as measured by the mRNA-transport assay was immunoprecipitated using polyclonal anti-rat p65 antibodies from the serum of rabbits immunized against the rat transplantable hepatocellular carcinoma THC 1682. This antibody removed activity from cytosols derived from Morris Hepatomas 7777 and 8994 and from cell culture media in which tumor cells were grown. Polyclonal anti-rat p65 antibodies reacted with human p65 secreted to the culture medium by the MCF-7 breast cancer cell line. The antibodies also cross-reacted with the mouse p65 factor secreted to medium by mouse squamous cell carcinoma. The p65 tumor-associated factor was not detected in the blood of pregnant rats. It was neither detected in the blood of normal rats nor in unconditioned cell culture medium.

EXAMPLE IV

CNBR Cleavage of p65

Cyanogen bromide (CNBR) cleavage maps of p65 purified from cell culture medium of rat transplantable hepatocellular carcinoma cell line 1682C or mouse liver carcinoma cell line CRL 6421 (MM45) were obtained as follows. p65 preparations (20µ) purified from cell culture medium were subjected to 12.5% sodium deodecyl sulfate (SDS)-PAGE. The p65 band located on slab gels by Coomassie blue staining of parallel gel tracks was cut from appropriate gel tracks and incubated at room temperature for 16 hours in 1 ml of 88% formic acid containing 20 mg/ml of CNBR. The gel slices were then rinsed five times with 1 ml of water and washed several times for 10 minutes with 1 ml 120 mM Tris-HCl, pH 7.0, 20% glycerol (vol/vol), 2% SOS until the pH of the slices reached 7.0. CNBr-treated gel slices were placed onto 15% SDS- PAGE slabs, electrophoresed, and then stained with silver. Slices of gel containing p65 treated with 88% formic acid served as controls.

Structural Identity of Rat and Mouse p65

Rat and mouse p65 were purified to apparent homogeneity as described above. CNBR cleavage maps were obtained as the first step toward the final characterization of the amino acid composition and sequence of p65. The cleavage of p65 with CNBR resulted in six major peptides identifiable by silver staining of the SDS-PAGE gels. The peptides have molecular weights of about 6, 9, 270, 39, 43 and 47 kDa. Identical cleavage maps were obtained for rat and mouse p65.

EXAMPLE V

Animal Models for Determination of Cancer Risk

The ultimate objective of animal carcinogenicity studies is the determination of possible human risk. The available data show that known human carcinogens that have been adequately studied are also carcinogenic in laboratory animals, often at the same target site. Thus, the identification and elucidation of the mechanisms underlying each stage of the carcinogenic process in animals may offer testable hypothesis for the stages in human. The current tests for cancer risk assessment focus mainly on markers of genetic damage, at the level of the DNA or chromosome, as indicators of genotoxic exposure. These tests, however, are not able to detect the risk associated with exposure to synthetic steroid hormones and other tumor promoters.

It was recently indicated that the promotional status of human subpopulations could be the dominant factor in determining the cancer risk. The development of a more systematic analysis of possible tumorigenesis mechanism has also been suggested. One of the approaches to study in a more systematic way the mechanism of tumorigenesis, involves comparisons among different systems in which tumor induction, or cell transformation has been optimized through the use of the most effective system-specific agents and protocols. When each tumor system is operating optimally, intersystem comparisons could be undertaken with respect to carefully selected biochemical parameters. Tumor-associated proteins, such as the one described herein which appears to be a general marker of preneoplastic and neoplastic alterations, are good candidates to be used in intersystem comparisons.

Monitoring Skin Carcinogenesis with p65 Tumor-Associated Factor

A multistage skin carcinogenesis model was used to monitor the carcinogenic process using the p65 tumor-associated marker.

Skin tumors were induced on the back of SENCAR mice by a single dose of 10 nmol of 7,12-dimethylbenz[a] anthracene (DMBA) and repetitive applications of 1 µg of 12-0-tetradecanoylphorbol-13-acetate (TPA) twice a week. Blood samples were randomly obtained from four mice at times indicated in FIG. 1. The p65 activity was measured in the blood plasma by use of an ELISA assay.

In a modified ELISA inhibition procedure, 100 µl of purified antigen of predetermined dilution was added to Dynatech Immunon 2 plates and incubated at 37° C. for one hour. This was followed by washing, then binding 1% bovine serum albumin in bicarbonate buffer to cover residual binding sites in the wells. After washing the plates, 100 µl of antiserum plus test samples were added and the incubation carried out for one hour at 37° C. Finally, the immune complex was detected by adding 100 µl of goat/anti-rabbit immunoglobulin conjugated to horseradish peroxidase. Then the substrate 2,21-Azino-(3-ethyl- benzthiazolinesulfonic acid) and 0.03% $H_2O_2$ was added to each well and incubated 10 minutes at room temperature. After terminating the reaction with addition of 20 ml of 2.0 mM $NaN_3$ to each well, the absorbance (405 nm) was read on an ELISA reader.

For convenience of graphing, the inhibition values were changed to units where the sample giving the greatest inhibition will be selected as the end point. The percent inhibition=100−[(Absorbance inhibited/absorbance uninhibited)×100]. The percent inhibition of the sample was multiplied by the reciprocal of the dilution to obtain units of the activity.

Figure 1A:
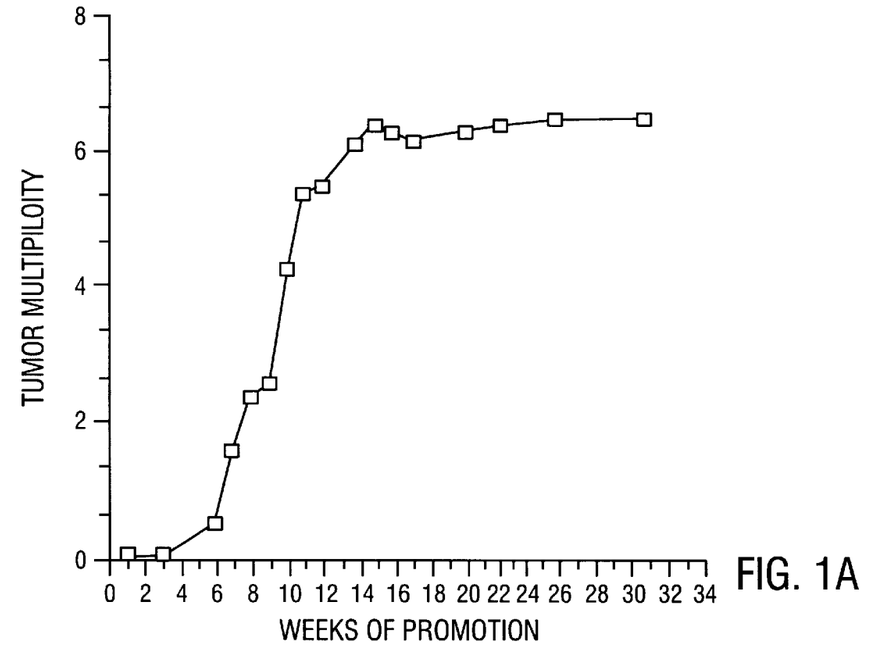
FIG. 1A shows the time course of papilloma appearance following carcinogenesis promotion and FIG. 1B shows the time course of p65 accumulation in the blood plasma following the same carcinogenesis promotion.
Figure 1B:
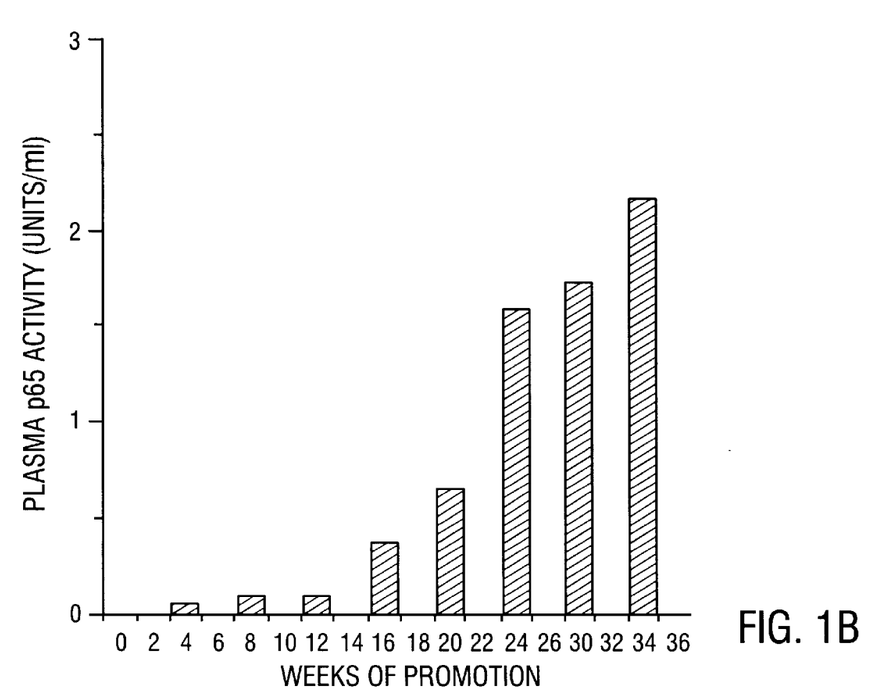

Shown in FIG. 1 was the time-course of (A) papilloma appearance and (B) p65 accumulation in the blood plasma. p65 was detected in the plasma at four weeks of promotion, then its activity increased, first slowly up to 20 weeks, and then more rapidly up to 30 weeks, when it began to plateau. p65 was not detected in the blood of non-initiated mice treated with TPA as described above up to 20 weeks (data not shown).

By using a simple blood test for the presence of p65 factor, the skin cancer risk from the tumor promoter TPA can be detected as early as four weeks of treatment with the tumor promoter. A majority of skin papillomas are considered to be non- malignant tumors at early stages of development. Conventional histological and cytogenetic techniques are time consuming and are able to detect skin cancers in mice only at later stages of papilloma development, i.e., at 30–40 weeks.

EXAMPLE VI

Monitoring Liver Carcinogenesis with p65 Tumor-Associated Factor

Altered hepatic foci (AHF) were induced in the course of 2-acetylaminofluorene (AAF)-initiated, phenobarbital (PB)-promoted hepatocarcinogenesis in the rat. Rats (male weanling albinos, Sprague Dawley strain) were purchased from Harlan Labs, Indianapolis, Ind. The 0.06% (w/w) AAF diet and 0.05% PB diet were prepared and pelleted by Altromin, Lage, FRG, and Dyets, Inc., Bethlehem, Pa., respectively. Each of two experimental groups of rats and a control group consisted of 40 rats. All rats entered the experiment at 22 days of age. One group received AAF diet for 18 days, then AIN-76A diet (Dyets, Inc.) The second group received AAF diet for 18 days then AIN-76A diet for 24 days and then AIN-76A diet supplemented with 0.05% phenobarbital. The third group (controls) received AIN-76A diet for 42 days, then AIN- 76A diet plus 0.05% phenobarbital.

Immunohistochemical Procedures

The blood and livers of rats (4 animals per each timepoint) sacrificed at different times in the course of hepatocarcinogenesis experiment were used for immunochemical studies. Paraffin liver sections were prepared and stained with specific antibodies. Polyclonal antibodies to the rat p65, purified to apparent homogeneity, were raised in rabbits as described herein. The p65 was visualized in the liver sections using the avidin- biotin-peroxidase complex (Vectastain ABC Kit, Vector Laboratories, Burlingame, Calif.). Appropriate controls with non-immune serum were performed routinely. Antiserum to p65 was diluted 1:200 in PBS with 1% goat serum for use in the staining protocol. The blood plasma was assayed for the presence of p65 using an ELISA assay or PAGE followed by immunoblotting analyses.

The p65 tumor-associated protein was detected in rats fed AAF and PB diets as early as two weeks of feeding with the tumor promoter PB. The p65 marker was predominantly present in the cells of putative preneoplastic foci found at 24 weeks of trial in livers of rats fed AAF and PB diets. The p65 marker was highly concentrated in the foci with little or none being detected in the surrounding cells. Either no staining or weak positive staining was found in the areas known for oval and ductular proliferation. No positive staining was found in control livers from normal rats or rats fed only the PB diet. Most of p65 activity appears to be associated with the nuclei of the p65-positive hepatocytes and more precisely with the nuclear envelopes, with relatively little being detected in the cytoplasm. Immunohistochemical staining of the cross-sectioned nuclei revealed that only the periphery of the nuclei, i.e., nuclear envelopes, were stained.

EXAMPLE VII

Enhancement of p65 Production During Sex Hormone Promotion

Figure 2:
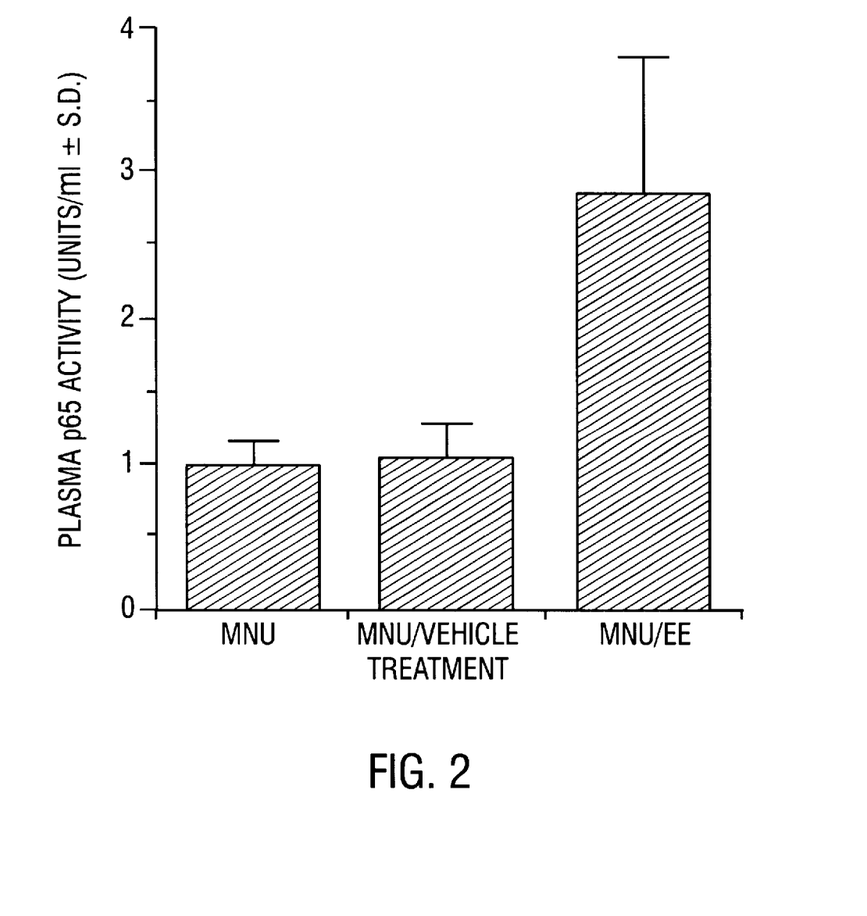
FIG. 2 shows enhancement by synthetic steroid hormone of p65 tumor-associated protein production during chemical carcinogenesis.

Shown in FIG. 2 is the effect of the contraceptive steroid ethynylestradiol (EE), a known tumor promoter in the rat, on the p65 production in female rats initiated with N-methyl-nitrosourea (MNU), using a protocol designed to induce mammary gland tumors.

A short (one week) exposure to EE at six to seven weeks post-carcinogen treatment, i.e., when the MNU-induced production of p65 was relatively low, caused three-fold increase of the p65 level in the blood plasma. MNU was shown to induce pre-neoplastic foci in the liver; however, they were not detected by the use of the gamma-glutamyl transpeptidase (GGT) assay, even after 23-week promotion with EE. Thus the 65 production in the rat appears to be extremely sensitive to hormonal stimulation. The high sensitivity of the p65 synthesis during chemical carcinogenesis to sex and phenobarbital promotion indicate that p65 can be used not only as a tumor marker, but also for early assessment of cancer risk associated with the use of synthetic steroids and other drugs that exhibit tumor promotion properties.

Evidence of resemblance of p65 to Steroid Receptors p65 amino acid sequence (SEQ ID NO: 2) deduced from the cDNA sequence. Blocks of zinc figure structures are underlined and SV40 translocation domain is double underlined. Fragments of the sequence in bold are peptide sequences obtained from the purified protein after CNBr cleavage.

```
  1  MDPENVRAEG  GDMREKVRLS  SARQRLRCST  KNSLLVARTC  VLRLVDWIEQ

51  DLKSTCEKAH  VSLRGYLELH  LQCGRRKEVA  GALGGDTRPD  PKKPRGGSKK

101  NVEDTLVKDK  LSPSSAVCES  PEVYGDDVGS  QAADSPRKQL  AAKGTFRDKD

151  KIEALFKLGE  LVAKKALSSA  ITWFPNSVSP  LHAHYGDEIL  YKDESGLVNI

201  SEGGKRGVEI  HPPDNFGITT  LDEDLGFPQI  IVINVKPQTE  EANTWLRQDL

251  KYHNSANEAG  YSDENKTFVR  GCRKDGHSER  NNMTTGDRNS  KKAQPVNFSL
```

```
301  MAS L AL DS RG   K AAG P R R GAR   R L C L V C E D Y A   S C S N T C V W S C   E A Y K V F F R R S

351  Q G N T D Y Y C F T  N D C N I  S K N R S  K S C P  AC L L RC   L H P S I  N E I  RK   D K R A A L N V R D

401  N V G E E V D MT G   P S WT C L K L L F   S D G E K V I  P R L   A H E L P G I  K R G   R Q A Q Q Q S H R G

451  S P I  P K K R K G W   P P G H V L S N D R   A A A G T V W K P K   S C E P I  R R E G P   K W D A R L N E S T

501  T F V L G S R A N K   A L G K G G T R G R   I Y I  K H P H L F K   Y A A D P Q D K H W   L A E Q H H R Q R F
```

Figure 3:
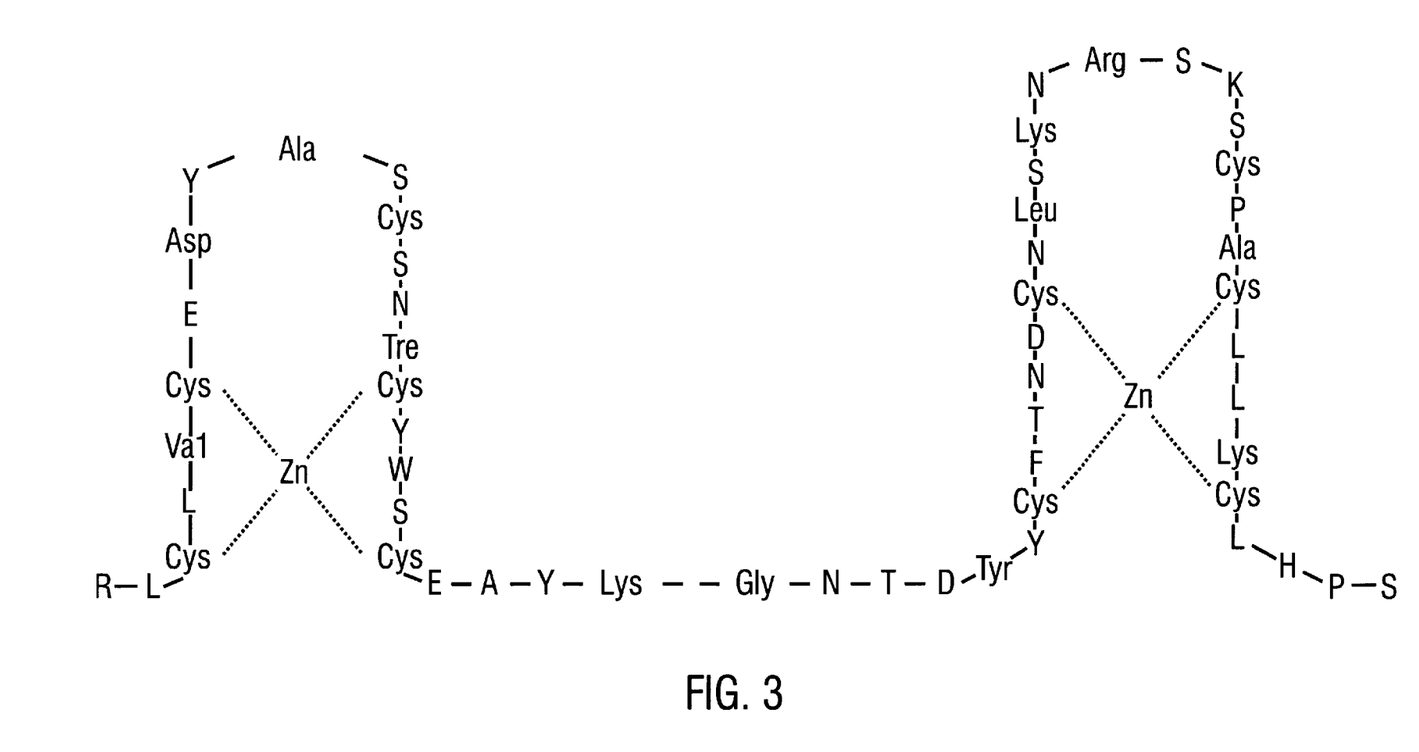
FIG. 3 shows zinc finger structure within p65. The amino acids abbreviated with three letters represent conserved regions of zinc fingers among family members.

Additional evidence that p65 may indeed belong to a superfamily of steroid receptors comes from the cloning and sequencing of rat p65 cDNA. The C-terminal end of p65 cDNA contains two sequences homologous to zinc fingers. Specifically, the sequence of the Cl region of p65 is very similar to several other steroid hormones. FIG. 3 depicts a proposed zinc finger structure of p65.

Post-translational modification of receptors is a possible mechanism by which receptor function can be regulated. Glucocorticoid, progesterone, estrogen and vitamin D receptors as well as p65 are phosphoproteins. The phosphorylation/dephosphorylation process is most likely a control mechanism for the regulation of transformation, hormone binding, DNA binding and transactivation. In addition, a prenylation site was found not very far from the C-terminal end. This is also post-translational modification by the attachment of either a farnesyl or geranyl/geranyl group to cysteine residues located at C-terminal extremity. Such modification is characteristic for several Ras and Ras-like proteins and nuclear lamins A and B as well as a number of G-proteins (transducins).

The intracellular localization of steroid receptors after synthesis has been studied extensively and it is proposed that cytoplasmic receptors bind hormone and rapidly translocate to the nucleus. This fact may explain immunostainings showing the presence of p65 not only in nuclei, but also in the cytoplasm in breast cancer tissues. Nuclear localization of proteins may occur by two different mechanisms. One is the diffusion of proteins through nuclear membrane; second, an interaction of proteins with the nuclear pores. This process is mediated by a translocation signal in the protein. Amino acid sequences having strong homology to the nuclear translocation signal of SV 40 T antigen have been found in several steroid receptors. The sequence above shows comparisons of highly homologous domains of translocation signal from human steroid receptors like GR, MR, AR, PR, ER and p65. These sequences, in the case of p65, are located close to the C-terminal site of the DNA-binding domain (Cl region), similarly to other receptor proteins in this family. It is still unknown, but is being actively studied, as to what serves as a ligand for p65.

The following examples describe in detail the protocols utilized to identify and sequence the p65 gene as well as to make hybridization probes for the identification of p65 protein in a sample.

EXAMPLE VIII

Cloning and Sequencing of the p65 gene

An H-35 Reuber hepatoma rat cDNA library was screened using rat anti-p65 monoclonal antibodies and have found to have several clones containing sequences homologous to p65, having approximately 1200 bp. Several hundred nucleotides (reverse and forward) from both sides of this cDNA was sequenced. p65 cDNA was cloned in plasmid pTA65Hum and used to transform $E.$ $coli$ JM 105 strains. Single-stranded templates were prepared and sequenced by the dideoxy chain-termination procedure (Messing J., Methods in Enzymology, 101: 20–78, 1983). The sequencing reaction was primed with either the universal primers or specific oligonucleotides complementary to sequence already determined (Strauss, E. C. et al., Anal . Biochem. 154: 353–360, 1986). The DNA sequences were analyzed with the GCG DNA Sequence Analysis Program. Initially, an 800–900 bp sequence data for the C-terminal end of the rat p65 cDNA (open reading frame) was obtained. Two polyadenylation signals (TTTAATT in p65 cDNA or AAAT-TAA in mRNA) and the poly A tail containing 18 As were found. Next, in the 1200 bp p65 cDNA fragment of p65 two fragments homologous to oligonucleotides backtranslated from the amino acid sequence of the p39 and p51 peptides of p65 were found. This was a strong confirmation that the proper cDNA fragment of p65 had been isolated. The nucleotide sequences were next assembled and analyzed with GeneJockey and DNA Strider softwares (Biosoft, Cambridge, UK). The sequence similarities were searched by GCG package through GeneBank and Owl data bases.

Hybrid p65-like proteins encoded by recombinant clones were induced with IPTG. Lysates were prepared and analyzed by SDS-PAGE gel electrophoresis and Western blot assay. The anti-p65 MAbs revealed immunoreactivity with respective β-galactosidase/p65 fusion proteins, as indicated by immunoblot analysis on bacterial cell extracts. MAbs were unreactive with other antigens present in different bacterial lysates and with β-galactosidase alone in pBluescript plasmid. The p65-like bacterial product was found to have molecular mass of 36 kDa as determined by Coomassie-blue-stained SDS-PAGE gel. These findings supported the theory that this cDNA clone coded for a fragment of the desired antigen.

It should be emphasized that the p65-like products, reacted identically with both monoclonal and polyclonal anti-p65 antibodies in immunoblotting experiments.

Sequencing efforts were continued in order to obtain the full sequence of the 1200 bp cDNA fragment. Because p65 has a molecular weight 65 kDa, the expected length of the clone containing rat p65 cDNA was estimated to be approximately 2000 bp. As discussed above, initial screening attempts, using monoclonal antibodies, to obtain the full cDNA sequence were not successful. Specifically, only fragments of the p65 gene with the C-terminal end or close to the C-terminal end were determinable. The N-terminal end (approximately 800 bp) was always missing. Therefore, a RACE PCR protocol was used to obtain the missing sequences. This protocol eventually resulted in the determination of the full cDNA sequence of rat p65 shown in SEQ ID NO: 1. The p65 amino acid sequence deduced from the cDNA sequence is shown in SEQ ID NO: 2.

PCR amplification of 5'-end p65 cDNA

5' AmpliFINDER anchor primer (CLONTECH Laboratories, Inc.) and specific to p65 cDNA antisense primer 5'CAGGTCCAGCTAGGACCGGG3' was used for amplification of the 5' end of p65 cDNA. Maximum amplification specificity was obtained using "hot start" PCR (D'Aquila, R. T., Nucleic Acids Res. 19: 3749, 1991). PCR reactions were carried out as described (Sambrook J. et al., Molecular Cloning : A Laboratory Manual, Cold Spring Harbor Laboratory, Cold Spring Harbor, N.Y., 1989). Amplification product was analyzed by agarose electrophoresis and Southern hybridization. Selected PCR product was purified from the acrylamide gel and cloned into TA vector, using TA cloning kit from Invitrogen Co. p65 inserts after EcoRI digestion recombined TAH10 plasmid were recloned into Bluscript II KS at EcoRI site.

Southern blot analysis

Amplification products were fractionated by electrophoresis in 1% agarose gel containing 1×TAE buffer (40 mM Tris-HCl, 18 mM NaCl, 20 mM sodium acetate, and 2 mM EDTA) after alkaline denaturation (Freeman M. R., Cancer Res., 49: 6221–6225, 1989). DNA was transferred from agarose gel to nitrocellulose (Schleicher & Schuell) according to Southern (Southern, E. M., J . Mol. Biol., 98 : 503–518, 1975). The membrane was baked for 2 h at 80° C. and prehybridized in a hybridization buffer (5×SSC, 5×Denhardt's solution, 10% dextran sulfate, 1% SDS, 20 μg/ml of salmon sperm DNA in 50% formamide) in 42° C., then hybridized with [$^{32}$P]-random primed cDNA probe overnight at the same temperature. After hybridization, the membrane was washed in 2×SSC at room temperature for 30 min. and then the membrane was washed under high stringency conditions (0.5×SSC, 1% SDS ) at 65° C. for 15 min. Autoradiography was performed using Hyperfilm™-MP from Amersham with the intensifying screen at −80° C.

Expression of the p65 Gene in Recombinant Vectors

After identifying and isolating the p65 DNA molecule, it may be inserted into any one of the many vectors currently known in the art and transferred to a prokaryotic or eukaryotic host cell where it will direct the expression and production of the so-called recombinant version of the protein.

A technique often employed by those skilled in the art of protein production today is to obtain a so-called "recombinant" version of the protein, to express it in a recombinant cell and to obtain the protein from such cells. To achieve this, a specific oligonucleotide based upon the sequence of the desired peptide, as is known to those of skill in the art and described herein is prepared. The oligonucleotide is then inserted into an expression vector, such as any one of the many expression vectors currently available commercially. A prokaryotic or eukaryotic host cell is then transformed with the vector, where it will direct the expression of the so-called recombinant version of the peptide, which may then be purified from the recombinant host cell. The preparation of oligonucleotide, vector and transformation of the host cell are within the skill of the ordinary artisan and is described in detail in Sambrook et al. (1989).

Particularly useful vectors are contemplated to be those vectors in which the coding portion of the DNA segment, whether encoding a full length protein or smaller peptide, is positioned under the control of a promoter. The promoter may be in the form of the promoter that is naturally associated with a p65 gene, e.g., in p65 tumor associated cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a rat p65 tumor marker gene in its natural environment. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides.

As mentioned above, in connection with expression embodiments to prepare recombinant rat p65 proteins and peptides, it is contemplated that longer DNA segments will most often be used, with DNA segments encoding the entire p65 protein being most preferred. However, it will be appreciated that the use of shorter DNA segments to direct the expression of shorter peptides or epitopic core regions, such as may be used to generate antibodies, also falls within the scope of the invention. Single stranded DNA molecules coding for the p65 protein can then be created and subsequently sequenced by the dideoxy chain termination procedure as described in Messing (1983). In addition, fragments may be expanded through the use of PCR technology of U.S. Pat. No. 4,603,102 (incorporated herein by reference).

Nucleic Acid Sequence of the p65 Molecule

Important aspects of the present invention concern isolated DNA segments and recombinant vectors encoding the 65 kDa oncofetal protein, and the creation and use of recombinant host cells through the application of DNA technology, that express this 65 kDa tumor marker protein.

As used herein, the term "DNA segment" refers to a DNA molecule that has been isolated free of total genomic DNA of a particular species. Therefore, a DNA segment encoding the rat p65 oncofetal protein refers to a DNA segment that contains p65 coding sequences yet is isolated away from, or purified free from, total genomic DNA of the rat. Included within the term "DNA segment", are DNA segments and smaller fragments of such segments, and also recombinant vectors, including, for example, plasmids, cosmids, phage, viruses, and the like.

Similarly, a DNA segment comprising an isolated or purified rat p65 gene refers to a DNA segment including p65 coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express proteins, polypeptides or peptides.

Isolated substantially away from other coding sequences" means that the gene of interest, in this case p65, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In preferred embodiments, the invention concerns isolated DNA segments and recombinant vectors incorporating DNA sequences that encode the rat p65 oncofetal protein comprising a sequence region having the sequence of SEQ ID NO: 1

The term "comprising a sequence region having the sequence of SEQ ID NO: 1" means that the sequence substantially corresponds to a portion of SEQ ID NO: 1 and has relatively few amino acids that are not identical to the amino acids of SEQ ID NO: 1. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO: 1 will be sequences that "comprising a sequence region having the sequence of SEQ ID NO: 1". The most preferred embodiment of the present invention consists of a protein molecule of SEQ ID NO: 1.

Naturally, where the DNA segment or vector encodes a full length p65 protein, or is intended for use in expressing the p65 protein, the most preferred sequences are those that are essentially as set forth in SEQ ID NO: 1 and that encode a protein that retains immunologic activity, e.g., as may be determined by the antibody assay, as disclosed herein.

Sequences Complementary to the p65 Molecule

Naturally, the present invention also encompasses DNA and RNA segments that are complementary, or essentially complementary, to the sequence set forth in SEQ ID NO: 1. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO: 1 under relatively stringent conditions such as those described herein in Example 10.

Amino Acid Sequence of the p65 Protein Molecule

In certain other embodiments, the invention concerns the rat p65 protein having the sequence of SEQ ID NO: 2. The term "having the sequence of SEQ ID NO: 2" is used in the same sense as described above and means that the nucleic acid sequence substantially corresponds to a portion of SEQ ID NO: 2 and has relatively few codons that are not identical, or functionally equivalent, to the codons of SEQ ID NO: 2. The term "functionally equivalent codon" is used herein to refer to codons that encode the same amino acid, such as the six codons for arginine or serine, and also refers to codons that encode biologically equivalent amino acids. The term "functionally equivalent codon" is well understood in the art.

Certain amino acids can be substituted for other amino acids in a sequence without appreciable loss of immunologic activity.

In making such changes, the hydropathic index of amino acids can be considered. The importance of the hydropathic amino acid index in conferring interactive biologic function on a peptide is generally understood in the art (Kyte & Doolittle, *J. Mol. Biol,* 157:105–132, 1982). It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is understood in the art that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent peptide thereby created is intended for use in immunological embodiments. U.S. Pat. No. 4,554,101, incorporated herein by reference, states that the greatest local average hydrophilicity of a peptide, as governed by the hydrophilicity of its adjacent amino acids, correlates with its immunogenicity and antigenicity, i.e. with a biological property of the peptide.

As detailed in U.S. Patent 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See table below). The present invention thus contemplates functional or biological equivalents of a peptide inhibitor of plasminogen activator inhibitor-1 as set forth above.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following examples are given by way of illustration, without intent to limit the scope of the invention, to show details of particularly preferred reagents and techniques utilized in the processes of the instant invention.

EXAMPLE IX

Creation of Hybridization Probes

Another important aspect of this invention resulting from the sequencing of the p65 protein is the ability to make and use hybridization probes for use in the detection of cancer.

The use of a hybridization probe of about 10–14 nucleotides in length allows the formation of a duplex molecule that is both stable and selective. One might also prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO: 1 and to select any continuous portion of the sequence, from about 10–14 nucleotides in length up to and including the full length sequence, that one wishes to utilize as a probe or primer. The choice of probe and primer sequences may be governed by various factors, such as, by way of example only, one may wish to employ primers from towards the termini of the total sequence, or from the ends of the functional domain-encoding sequences, in order to amplify further DNA; one may also employ probes corresponding to regions of the entire DNA that are homologous to genes from any species including human in order to screen for cancer.

Accordingly, the nucleotide sequences of the invention may be used for their ability to selectively form duplex molecules with complementary stretches of p65 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating rat p65 genes.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

p65 mRNA-specific oligonucleotide probes may be used for detecting proliferating cells like cancerous cells in tissue/cell samples. The steps include (a) preparation of tissue/cell sample; (b) hybridization with cocktail of non-radioactively, or radioactively labeled oligonucleotide probes for p65 mRNA; and (c) detecting the presence of p65 probe hybrids.

EXAMPLE X

Antisense Technology

Inhibition of gene function with antisense nucleotides may have some therapeutic utility. Therefore, series of antisense phosphorothioate oligonucleotides complementary to the p65 nucleotide sequence were prepared that can be used to inhibit expression of the p65 gene in breast, ovary and prostate cancer cell lines, as well as other cancer cell lines. The oligonucleotides are effective only when complexed with Lipofectin and the level of expression may be reduced by approximately 50–80%. In experiments with the antisense expression the steady-state level of mRNA is reduced. Antisense therapy using small oligonucleotide antisense molecules of p65 mRNA or DNA as well as or defective retrovirus or adenovirus carrying the antisense ribo- or deoxy-sequences of p65, respectively, may be very effective in the prevention and or treatment of cancer.

REFERENCES CITED

1. Mirowski, M., Sherman, U., and Hanausek, M. Purification and characterization of a 65-kDa tumor-associated phosphoprotein from rat transplantable hepatocellular carcinoma 16820cell line. *Protein Expression and Purification,* 3:196–203, 1992.
2. Wang, S., Mirowski, M., Sherman, U., Walaszek, Z., and Hanausek, M. Monoclonal antibodies against a 65 kDa tumor-associated phosphoprotein: development and use in cancer detection. *Hybridoma,* 12:167–176, 1993.
3. Mirowski, M., Walaszek, Z., Sherman, U., Adams, A. K. and Hanausek, M. Demonstration of a 65 kDa tumor-specific phosphoprotein in urine and serum of rats with N-methyl-N-nitrosourea-induced mammary adenocarcinoma. *Carcinogenesis* 14:8, 1659–1664, 1993.
4. Mirowski, M., Walaszek, Z., Sherman, U., Adams, A. K. and Hanausek, M. Comparative structural analysis of human and rat 65 kDa phosphoprotein. *Int. J. Biochem.,* 25:1865–1871, 1993.
5. Del Rio, M., Hanausek M., Walaszek, Z. and Stoica, G. Expression of a 65 kDa oncofetal phosphoprotein in the altered hepatic foci of rats fed 2-acetylaminofluorene followed by phenobarbital. *Int. J. Oncology* 5:259–265, 1994.
6. Mirowski, M., Klijanienko, J., Wang, S., Vielh, P., Walaszek, Z. and Hanausek, M. Serological and immunohistochemical detection of a 65 kDa protein breast cancer. *Eur. J. Cancer.,* 30A:1108–1113, 1994.
7. Southern, E. M. Detection of specific sequences among DNA fragments separated by gel electrophoresis. *J. Mol. Biol.,* 98:503–518, 1975.
8. Freeman M. R., Washecka, R., and Chung L. W. K. Aberrant expression of epidermal growth factor receptor and Her-2 (erbB-2) messenger RNAs in human renal cancers. *Cancer Res.,* 49:6221–6225, 1989.
9. Strauss, E. C. et al., Use of the universal primers or specific oligonucleotides complementary to sequences already determined. *Anal. Biochem.* 154:353–360, 1986.
10. Messing J. A system for shotgun DNA sequencing. *Methods in Enzymology,* 101:20–78, 1983.
11. Sambrook J. et al., Molecular Cloning:A Laboratory Manual,Cold Spring Harbor Laboratory, Cold Spring Harbor, N.Y., 1989.

What is claimed is:

1. A nucleic acid molecule of less than 2200 base pairs (DNA) or less than 2200 bases (RNA) substantially free of other proteinaceous and nucleic acid materials, wherein said molecule is selected from the group consisting of:
   a. a DNA segment comprising a sequence region having the sequence of SEQ ID NO: 1; and
   b. an RNA segment comprising a sequence region having the sequence of SEQ ID NO: 1 with a proviso that in said RNA molecule, the deoxynucleotides A, G, C and T of SEQ ID NO: 1 are replaced by ribonucleotides A, G, C and U, respectively.

2. The nucleic acid molecule of claim 1 substantially free of other proteinaceous and nucleic acid materials, wherein said molecule is selected from the group consisting of:
   a. a DNA molecule having a sequence of SEQ ID NO: 1; and
   b. an RNA molecule having a sequence of SEQ ID NO: 1 with a proviso that said RNA molecule, the deoxynocleotides A, G, C and T of SEQ ID NO: 1 are replaced by ribonucleotides A, G, C and U, respectively.

3. The nucleic acid molecule of claim 1, wherein said molecule is a DNA segment and is under the control of a promoter.

4. The nucleic acid molecule of claim 1, wherein said molecule is a DNA segment and is incorporated into a DNA plasmid.

5. The nucleic acid molecule of claim 1, wherein said molecule is a DNA segment incorporated into a host cell to form a recombinant host cell.

6. The host cell of claim 5, further defined as a prokaryotic host cell.

7. The host cell of claim 6, wherein the prokaryotic cell is *E. coli*.

8. The host cell of claim 5, further defined as a eukaryotic host cell.

9. A protein molecule substantially free of other proteinaceous and nucleic acid materials, said protein molecule having the amino acid sequence of SEQ ID NO: 2.

10. A method of using a DNA segment having the sequence of SEQ ID NO: 1 comprising the steps of:
    a. preparing a recombinant vector in which the sequence region having the sequence of SEQ ID NO: 1 is positioned under the control of a promoter;
    b. introducing said recombinant vector into a host cell to generate a recombinant host cell;
    c. culturing the recombinant host cell under conditions effective to allow expression of the protein encoded by the sequence region having the sequence of SEQ ID NO: 1; and
    d. collecting the protein encoded by SEQ ID NO: 1.

11. A recombinant p65 protein prepared by expressing SEQ ID NO: 1 in a recombinant host cell in accordance with claim 10 and purifying the expressed protein away from total recombinant host cell components.

12. A nucleic acid molecule comprising a sequence region that consists of at least a 20 nucleotide long continuous sequence that hybridizes under stringent conditions to a contiguous sequence of SEQ ID NO: 1 from nucleic acid position 1 to nucleic acid position 1035.

13. A method for detecting the presence of nucleic acids encoding for the p65 oncofetal protein in a mammalian sample, comprising the steps of:
    a. obtaining nucleic acids from a sample suspected of containing the p65 oncofetal protein;
    b. isolating nucleic acids from said sample;
    c. contacting said nucleic acids with a nucleic acid segment of at least a 20 nucleotide long continuous sequence that hybridizes under stringent conditions to a contiguous sequence of SEQ ID NO: 1 from nucleic acid position 1 to nucleic acid position 1035 under conditions effective to allow hybridization of substantially complementary nucleic acids; and
    d. detecting the hybridized complementary nucleic acids thus formed.

14. The method of claim 13, wherein the sample nucleic acids contacted are located within a cell.

15. The method of claim 13, wherein the sample nucleic acids are separated from a cell prior to contact.

16. The method of claim 15, wherein the sample nucleic acids are DNA.

17. The method of claim 15, wherein the sample nucleic acids are RNA.

18. A method to aid in the diagnosis of a cancer which produces a 65 kD tumor-associated protein in a mammal comprising:

a. providing a sample of nucleic acids from the biological material of said mammal wherein the biological material is plasma, serum, urine, saliva, cystol fluid, ascites or tissue;

b. contacting said sample nucleic acids with a nucleic acid segment of at least a 20 nucleotide long continuous sequence that hybridizes under stringent conditions to a contiguous sequence of SEQ ID NO: 1 from nucleic acid position 1 to nucleic acid position 1035 under conditions effective to allow hybridization of substantially complementary nucleic acids; and c. detecting the hybridized complementary nucleic acids thus formed.

19. A method for detecting p65 oncofetal protein in a mammalian sample comprising the steps of:

a. preparing an antibody preparation to a purified protein p65 of claim 9;

b. selecting an antibody set that is immunoreactive to p65 protein, and not immunoreactive to estrogen receptor protein;

c. providing a mammalian sample comprising plasma, serum, urine, saliva, cystic fluid, ascites, or tissue;

d. contacting said sample and said antibody set to form an immunoconjugate; and e. detecting said immunoconjugate.

20. The method of claim 19, wherein said antibody preparation is polyclonal, monoclonal, or monospecific.

21. The nucleic acid molecule of claim 12, further defined as having the sequence of SEQ ID NO: 1.

22. The method of claim 13, wherein the nucleic acid segment has the sequence of SEQ ID NO:1.

23. A method for detecting p65 oncofetal protein in a mammalian sample comprising the steps of:

a. preparing an antibody preparation to the N-terminal half of the p65 protein;

b. providing a mammalian sample comprising plasma, serum, urine, saliva, cystic fluid, ascites, or tissue;

c. contacting said sample and said antibody preparation to form an immunoconjugate; and d. detecting said immunoconjugate.

24. The method of claim 23, wherein said antibody preparation is polyclonal, monoclonal, or monospecific.

* * * * *

UNITED STATES PATENT AND TRADEMARK OFFICE
CERTIFICATE OF CORRECTION

| | | |
|---|---|---|
| PATENT NO. | : 5,773,215 | Page 1 of 1 |
| APPLICATION NO. | : 08/405648 | |
| DATED | : June 30, 1998 | |
| INVENTOR(S) | : Margaret Hanausek-Walaszek et al. | |

It is certified that error appears in the above-identified patent and that said Letters Patent is hereby corrected as shown below:

In column 1, lines 15-17, please delete "The United States Government may have certain rights to this invention pursuant to National Institutes of Health grants RR 5511-23 and CA 54296" insert --This invention was made with government support under CA054296 and RR005511 awarded by the National Institutes of Health. The government has certain rights in the invention.-- therefor.

Signed and Sealed this

First Day of April, 2008

JON W. DUDAS
*Director of the United States Patent and Trademark Office*